(12) United States Patent
Lestienne et al.

(10) Patent No.: US 6,972,683 B2
(45) Date of Patent: Dec. 6, 2005

(54) BADGE FOR A LOCATING AND TRACKING SYSTEM

(75) Inventors: James Lestienne, Chapel Hill, NC (US); Paul J. McDaniel, III, Burlington, KY (US); Richard J. Schuman, Cary, NC (US); Dilbir S. Kalra, Cary, NC (US)

(73) Assignee: Hill-Rom Services, Inc., Wilmington, DE (US)

( * ) Notice: Subject to any disclaimer, the term of this patent is extended or adjusted under 35 U.S.C. 154(b) by 40 days.

(21) Appl. No.: 10/199,849

(22) Filed: Jul. 19, 2002

(65) Prior Publication Data

US 2003/0090387 A1 May 15, 2003

Related U.S. Application Data

(60) Provisional application No. 60/306,818, filed on Jul. 20, 2001.

(51) Int. Cl.[7] ............................................. G08B 13/14
(52) U.S. Cl. ................. 340/572.1; 340/572.4; 340/572.8; 340/573.1; 340/539.1; 340/825.49; 340/825.69; 340/825.72
(58) Field of Search ..................... 340/825.49, 825.36, 340/825.69, 825.52, 572.1, 572.4, 572.8, 340/573.1, 573.4, 572.7, 539.1, 825.54, 825.72, 340/825.34, 825.46

(56) References Cited

U.S. PATENT DOCUMENTS

| 3,439,320 A | 4/1969 | Ward |
| 3,739,329 A | 6/1973 | Lester |
| 4,151,407 A | 4/1979 | McBride et al. |
| 4,216,462 A | 8/1980 | McGrath et al. |
| 4,225,953 A | 9/1980 | Simon et al. |
| 4,275,385 A | 6/1981 | White |
| 4,443,693 A * | 4/1984 | Berezowski et al. ........ 235/458 |
| 4,601,064 A | 7/1986 | Shipley |
| 4,649,385 A | 3/1987 | Aires et al. |
| 4,728,928 A | 3/1988 | Shipley |
| 4,759,022 A | 7/1988 | Akerberg |
| 4,837,568 A | 6/1989 | Snaper |
| 4,906,853 A | 3/1990 | Linwood et al. |
| 4,967,195 A | 10/1990 | Shipley |
| 4,979,217 A | 12/1990 | Shipley |
| 4,990,892 A | 2/1991 | Guest et al. |
| 5,017,794 A | 5/1991 | Linwood et al. |
| 5,027,314 A | 6/1991 | Linwood et al. |
| 5,051,741 A | 9/1991 | Wesby |

(Continued)

FOREIGN PATENT DOCUMENTS

GB          2 193 359          2/1988

(Continued)

OTHER PUBLICATIONS

"Great New Product: Infrared Locator," Teleconnect, Feb., 1986.

(Continued)

*Primary Examiner*—Hung Nguyen
(74) *Attorney, Agent, or Firm*—Bose McKinney & Evans LLP

(57) ABSTRACT

A badge (26) for locating and tracking a hospital asset (11) includes a motion sensor (30) carried by the asset (11) that generates a motion signal when the asset (11) is in motion. The motion signal varies with changes in the speed of the moving asset (11). The badge (26) further includes a transmitter (34) coupled to the motion sensor (30) that transmits an information signal at a transmission rate that varies as a function of the variable motion signal. The badge (26) may be configured to provide fault tolerant reception by transmitting information in packets including periodic error codes.

34 Claims, 6 Drawing Sheets

U.S. PATENT DOCUMENTS

| | | | |
|---|---|---|---|
| 5,062,151 | A | 10/1991 | Shipley |
| 5,119,104 | A * | 6/1992 | Heller .................. 342/450 |
| 5,153,584 | A | 10/1992 | Engira |
| 5,214,421 | A | 5/1993 | Vernon et al. |
| 5,218,344 | A | 6/1993 | Ricketts |
| 5,260,840 | A | 11/1993 | Hatanaka et al. |
| 5,291,399 | A | 3/1994 | Chaco |
| 5,317,309 | A | 5/1994 | Vercellotti et al. |
| 5,319,363 | A | 6/1994 | Welch et al. |
| 5,341,412 | A | 8/1994 | Ramot et al. |
| 5,355,222 | A | 10/1994 | Heller et al. |
| 5,363,425 | A | 11/1994 | Mufti et al. |
| 5,387,993 | A | 2/1995 | Heller et al. |
| 5,390,238 | A | 2/1995 | Kirk et al. |
| 5,396,224 | A | 3/1995 | Dukes et al. |
| 5,402,469 | A | 3/1995 | Hopper et al. |
| 5,412,715 | A | 5/1995 | Volpe |
| 5,417,222 | A | 5/1995 | Dempsey et al. |
| 5,426,425 | A | 6/1995 | Conrad et al. |
| RE35,035 | E | 9/1995 | Shipley |
| 5,455,851 | A | 10/1995 | Chaco et al. |
| 5,458,123 | A | 10/1995 | Unger |
| 5,461,665 | A | 10/1995 | Shur et al. |
| 5,465,082 | A | 11/1995 | Chaco |
| 5,471,404 | A | 11/1995 | Mazer |
| 5,493,283 | A | 2/1996 | Hopper et al. |
| 5,500,651 | A * | 3/1996 | Schuermann .................. 342/42 |
| 5,515,426 | A | 5/1996 | Yacenda et al. |
| 5,534,876 | A | 7/1996 | Erickson et al. |
| 5,541,585 | A | 7/1996 | Duhame et al. |
| 5,548,637 | A | 8/1996 | Heller et al. |
| 5,561,412 | A | 10/1996 | Novak et al. |
| 5,572,195 | A | 11/1996 | Heller et al. |
| 5,576,952 | A | 11/1996 | Stutman et al. |
| 5,588,009 | A | 12/1996 | Will |
| 5,594,786 | A | 1/1997 | Chaco et al. |
| 5,627,524 | A | 5/1997 | Fredrickson et al. |
| 5,633,742 | A | 5/1997 | Shipley |
| 5,682,142 | A * | 10/1997 | Loosmore et al. ....... 340/572.1 |
| 5,689,229 | A | 11/1997 | Chaco et al. |
| 5,699,038 | A | 12/1997 | Ulrich et al. |
| 5,732,711 | A | 3/1998 | Fitzpatrick et al. |
| 5,742,233 | A | 4/1998 | Hoffman et al. |
| 5,745,037 | A | 4/1998 | Guthrie et al. |
| 5,745,272 | A | 4/1998 | Shipley |
| 5,793,861 | A | 8/1998 | Haigh |
| 5,815,566 | A | 9/1998 | Ramot et al. |
| 5,818,617 | A | 10/1998 | Shipley |
| 5,822,418 | A | 10/1998 | Yacenda et al. |
| 5,822,544 | A | 10/1998 | Chaco et al. |
| 5,835,023 | A | 11/1998 | Ito et al. |
| 5,838,223 | A | 11/1998 | Gallant et al. |
| 5,838,698 | A | 11/1998 | Doubler et al. |
| 6,009,333 | A | 12/1999 | Chaco |
| 6,104,295 | A | 8/2000 | Gaisser et al. |
| 6,133,837 | A | 10/2000 | Riley |
| 6,147,592 | A | 11/2000 | Ulrich et al. |
| 6,198,394 | B1 * | 3/2001 | Jacobsen et al. ......... 340/573.1 |
| 6,211,790 | B1 | 4/2001 | Radomsky et al. |
| 6,252,512 | B1 | 6/2001 | Riley |
| 6,259,355 | B1 | 7/2001 | Chaco et al. |
| 6,344,794 | B1 | 2/2002 | Ulrich et al. |

FOREIGN PATENT DOCUMENTS

| | | |
|---|---|---|
| GB | 2 230 365 | 10/1990 |
| GB | 2 265 038 | 9/1993 |
| JP | 2028581 | 9/1989 |
| JP | 6186316 | 7/1994 |
| JP | 10038603 | 2/1998 |
| WO | WO/9501014 | 1/1995 |
| WO | WO/9934341 | 7/1999 |
| WO | WO 01/33748 | 5/2001 |
| WO | WO/0133748 | 5/2001 |
| WO | WO 01/46711 | 6/2001 |
| WO | WO/0146711 | 6/2001 |

OTHER PUBLICATIONS

T.H. Ooi, "Low Cost RF Identification and Locating System," IEEE Trans. On Consumer Electronics, vol. 35 No. 4, Nov. 1989, pp. 831-839.

United Identifications Systems Corp., Infra-Corp., 1989.

The Computer for the 21st Century, Mark Weiser, Scientific American, Sep. 1991.

Keeping Track of Alzhemier and Dementia Prone Patients Just Got Easier, Security Tag Systems, Inc., 1991.

Infant Monitoring System, Sekurmed.

* cited by examiner 2.2 μSEC

|← 26.4 μSEC = BIT ON TIME (HI) →|

2.2 μSEC

|← 26.4 μSEC = BIT ON TIME (LO) →|

FIG. 9

66 μSEC = TOTAL BIT TIME FOR ONE DATA BIT
26.4 μSEC = BIT ON TIME
39.6 μSEC = BIT SPACING TIME

FIG. 10

| STOP BIT | 1 | | |
|---|---|---|---|
| PARITY BIT | 1 | | |
| FUTURE BITS | 0 | INACTIVE | |
| | 0 | | |
| | 0 | | |
| PARITY BIT | 1 | | |
| DEVICE TYPE BITS | 0 | INACTIVE | |
| | 0 | | |
| | 0 | | |
| PARITY BIT | 0 | | |
| LOW BATT. BITS | 1 | ACTIVE | |
| | 1 | | |
| | 1 | | |
| PARITY BIT | 0 | | |
| REMOTE NOTIF. BITS | 1 | ACTIVE | |
| | 1 | | |
| | 1 | | |
| PARITY BIT | 1 | | |
| ID BITS - HI BYTE | 0 | 5 | < MSB |
| | 1 | | |
| | 0 | | |
| | 1 | | |
| | 0 | A | |
| | 1 | | |
| | 0 | | |
| | 0 | | |
| PARITY BIT | 0 | | |
| ID BITS - LO BYTE | 0 | 6 | |
| | 1 | | |
| | 1 | | |
| | 0 | | |
| | 1 | D | |
| | 1 | | |
| | 0 | | |
| | 1 | | |
| FRAMING BIT | 1 | | < LSB |
| START BIT | 1 | | |

BADGE FOR A LOCATING AND TRACKING SYSTEM

This application claims the benefit of U.S. Provisional Application No. 60/306,818, filed Jul. 20, 2001, which is incorporated by reference herein.

BACKGROUND AND SUMMARY OF THE INVENTION

This invention relates generally to systems for locating and tracking personnel and equipment within a facility and more particularly to a system wherein a portable transmitter transmits identification information at a transmission rate that varies as a function of the speed of movement of the transmitter.

Systems for monitoring the location of hospital personnel and equipment are known. One monitoring approach is taught in U.S. Pat. No. 4,275,385 to White, which is incorporated herein by reference. White discloses a personnel locating system where individuals to be located wear infrared transmitters which transmit a pulse-coded signal that identifies the wearer. Other systems, for example the systems taught in U.S. Pat. No. 5,561,412 to Novak et al.; U.S. Pat. No. 5,699,038 to Ulrich et al.; and U.S. Pat. No. 5,838,223 to Gallant et al., all of which are incorporated herein by reference, disclose the use of infrared signaling in communications systems that integrate several aspects of personnel and equipment locating, call/code enunciation, and equipment status information.

Most conventional locating and/or tracking systems in hospitals use infrared ("IR") and/or radio frequency ("RF") technology. In such systems, badges (or "tags") are attached to personnel and to movable assets such as equipment. The badges typically transmit unique identification signals to receivers that are stationed at various fixed locations throughout the hospital. Generally, a reception of an identification signal from a particular badge by a particular receiver indicates the location of a particular asset. As such, typical hospital locating and tracking systems have a "static resolution" (i.e., the capability to determine with a particular accuracy the location of a stationary asset), and a "dynamic resolution" (i.e., the capability to determine with a particular accuracy the location of an asset as it moves through the hospital).

Static resolution may be increased by increasing the number of receivers within a particular area. For example, if a wing has twelve patient rooms, then a system having a receiver in each room will more accurately indicate the location of a nurse than will a system with only one receiver at an entrance to the wing. Dynamic resolution, however, also depends on how frequently the badges transmit their identification signals. Further, the transmission rate required to support a high dynamic resolution for a particular asset is generally proportional to the speed of movement of the asset through the hospital. For example, consider again the wing that has a receiver in each of the twelve patient rooms. If a nurse randomly circulates through the wing at about five minutes per room (i.e., approximately one hour total of rounds), then a badge that transmits only once per hour will not provide as accurate an indication of the nurse's route or location as will a badge that transmits once every minute.

On the other hand, increasing the transmission rate of the badges generally increases the amount of transmission traffic in the system, thereby increasing the chances for data collisions and/or other transmission errors. For IR systems, common infrared noise sources such as the flourescent lights in a patient's room may also cause transmission errors. Moreover, increasing the transmission rate increases the number of transmissions from each badge over a given time period, thereby decreasing battery life or requiring higher capacity batteries, both of which are undesirably costly.

The present invention provides a badge configured to transmit identification signals for locating and tracking an asset in a hospital. The badge includes a motion sensor configured to generate a motion signal that corresponds to a speed of movement of the asset through the hospital. The badge also includes a transmitter coupled to the motion sensor to receive the motion signal from the motion sensor. The transmitter periodically transmits an information signal that identifies the asset at a transmission rate that corresponds to the motion signal.

In another alternative embodiment, the present invention provides an apparatus and method for fault-tolerant reception of a message packet in a hospital locating and tracking system. The method includes the steps of (a) checking for a synchronization signal; (b) receiving a first set of data bits; (c) receiving a first error code; (d) determining whether the first error code agrees with the first set of data bits; (e) checking for a stop signal upon a determination that the first error code agrees with the first set of data bits; (f) repeating steps (a)–(d) upon a determination that the first error code does not agree with the first set of data bits; (g) upon a determination that the stop signal has not been received: receiving a second set of data bits, receiving a second error code, determining whether the second error code agrees with the second set of data bits, checking for the stop signal upon a determination that the second error code agrees with the second set of data bits, repeating steps (a)–(g) upon a determination that the second error code does not agree with the second set of data bits; and (h) constructing a message packet that includes the first set of data bits and the second set of data bits upon a determination that the stop signal has been received.

The features of the present invention described above, as well as additional features, will be readily apparent to those skilled in the art upon reference to the following detailed description and the accompanying drawings.

BRIEF DESCRIPTION OF THE DRAWINGS

FIG. 6 is a graph depicting a vertical acceleration curve and a horizontal acceleration curve of the type generated by a badge according to the present invention;

FIGS. 7–9 are timing diagrams of signals generated by a badge according to the present invention;

FIG. 10 is a chart depicting a data packet and communications protocol for a signal generated by a badge according to the present invention.

DETAILED DESCRIPTION OF EMBODIMENTS OF THE INVENTION

The embodiments selected for description below are not intended to be exhaustive or to limit the invention to the precise forms disclosed. Rather, the embodiments were selected to enable one of ordinary skill in the art to practice the invention.

The present invention relates to a badge including a transmitter designed for use with a locating and tracking system such as the COMposer® communications system or COMLinx™ system available from Hill-Rom® of Batesville, Ind., some details of which are disclosed in U.S. Pat. Nos. 5,561,412; 5,699,038; and 5,838,223; all of which are incorporated herein by reference. Such systems typically use free-space infrared data transmission from badges and/or tags to receivers in a wall or ceiling of a hospital room. However, the present invention is not limited to use with any particular communications system.

Figure 1:
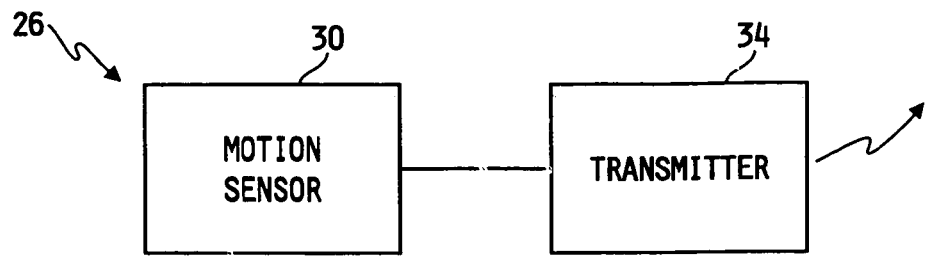
FIG. 1 is a functional block diagram for a badge according to the present invention.

Referring now to FIG. 1, a badge 26 according to the present invention generally includes a motion sensor 30 and a transmitter 34. The motion sensor 30 is configured to generate a motion signal that corresponds to a speed of movement of an "asset" through a hospital. The asset may be a person, a piece of equipment, or any other thing to be located and/or tracked. The motion signal may be based on a direct measurement of the speed or acceleration of the asset, a measurement of vibration of the asset, or any other parameter that may vary with the speed of movement of the asset. The transmitter 34 is coupled to the motion sensor 30 to receive the motion signal therefrom through an electrical connection or any other suitable coupling. The transmitter 34 periodically transmits an information signal at a transmission rate that correspond to the motion signal as is further described below.

Figure 3:
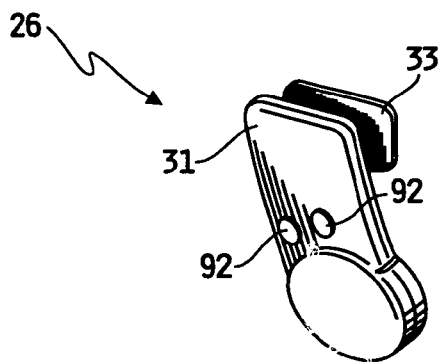
FIG. 3 is a perspective view of a badge according to the present invention.

As shown in FIG. 3, the badge 26 includes a housing 31, which is preferably made of molded plastic, two infrared LEDs 92 for transmitting the pulse-coded infrared information signals, and a fastener 33 that enables the badge 26 to be clipped to a piece of equipment or the clothing of a hospital worker. While fastener 33 is shown as a spring-biased clip, it should be understood that any suitable means for fastening badge 26 to the asset may be employed and is within the scope of the invention.

Figure 2:
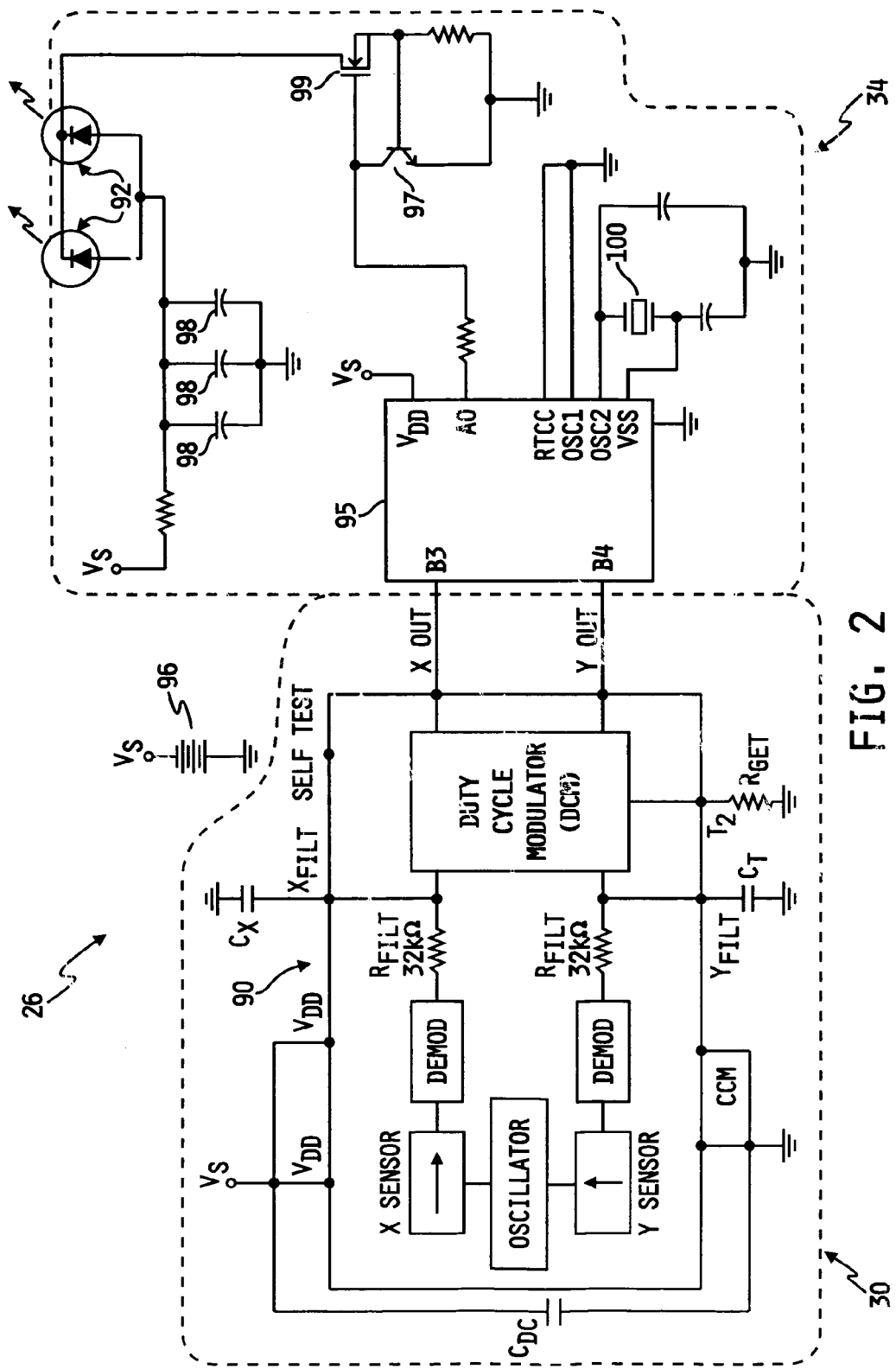
FIG. 2 is a schematic diagram of the badge of FIG. 1.

As shown in FIG. 2, the motion sensor 30 includes a dual axis accelerometer 90, with a measurement range, for example, of ±2 g, which generates the motion signal in response to accelerations of the asset to which the badge 26 is attached. The accelerometer 90 can measure both dynamic acceleration (e.g., vibration) and static acceleration (e.g., gravity). The outputs of the accelerometer 90 are Duty Cycle Modulated ("DCM") signals whose duty cycles (ratio of pulse width to period) are proportional to the acceleration in each of the two sensitive axes. These outputs form the motion signal and are measured directly by a microcontroller 95 included in the transmitter 34.

Transmitter 34 further includes two infrared LEDs 92, filter capacitors 98, a bipolar transistor 97, a FET 99, and a crystal oscillator 100, as well as various other passive components. Microcontroller 95 determines the approximate speed of movement of the asset from the motion signal and causes the transmitter 34 to periodically transmit the information signal at a transmission rate that corresponds to the speed of movement (which corresponds to the motion signal). To this end, the microcontroller 95 varies the transmission interval between message packets. The FET 99 and the bipolar transistor 97 drive the LEDs 92, which emit the information signal on the infrared carrier as is further described below.

Figure 4:
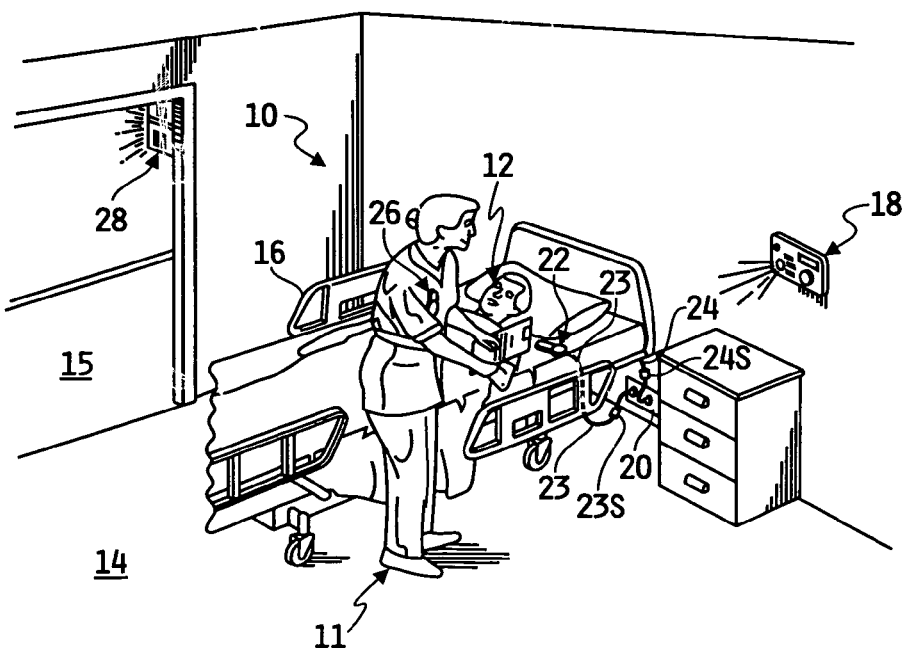
FIG. 4 is a perspective view of a nurse wearing a badge according to the present invention in a patient room of a hospital.

FIG. 4 shows a nurse 11 (as an example of an asset) wearing the badge 26 in a patient room 14 of a hospital. As mentioned above, the badge 26 periodically transmits a pulse-code infrared signal that includes a unique identification code for the nurse 11. An exemplary patient station 18 is mounted to a head wall of the patient room 14. The patient station 18 includes a receiver (not shown) that is configured to receive the identification code, and is coupled to the remaining components of a hospital locating and tracking system (not shown) which determine and continuously update the location of the nurse 11 within the hospital. Illustratively, the receiver is coupled to a remote computer such as a master nurse's station. The remote computer updates a database each time a signal is received from a receiver indicating a new location for the nurse 11.

Figure 5:
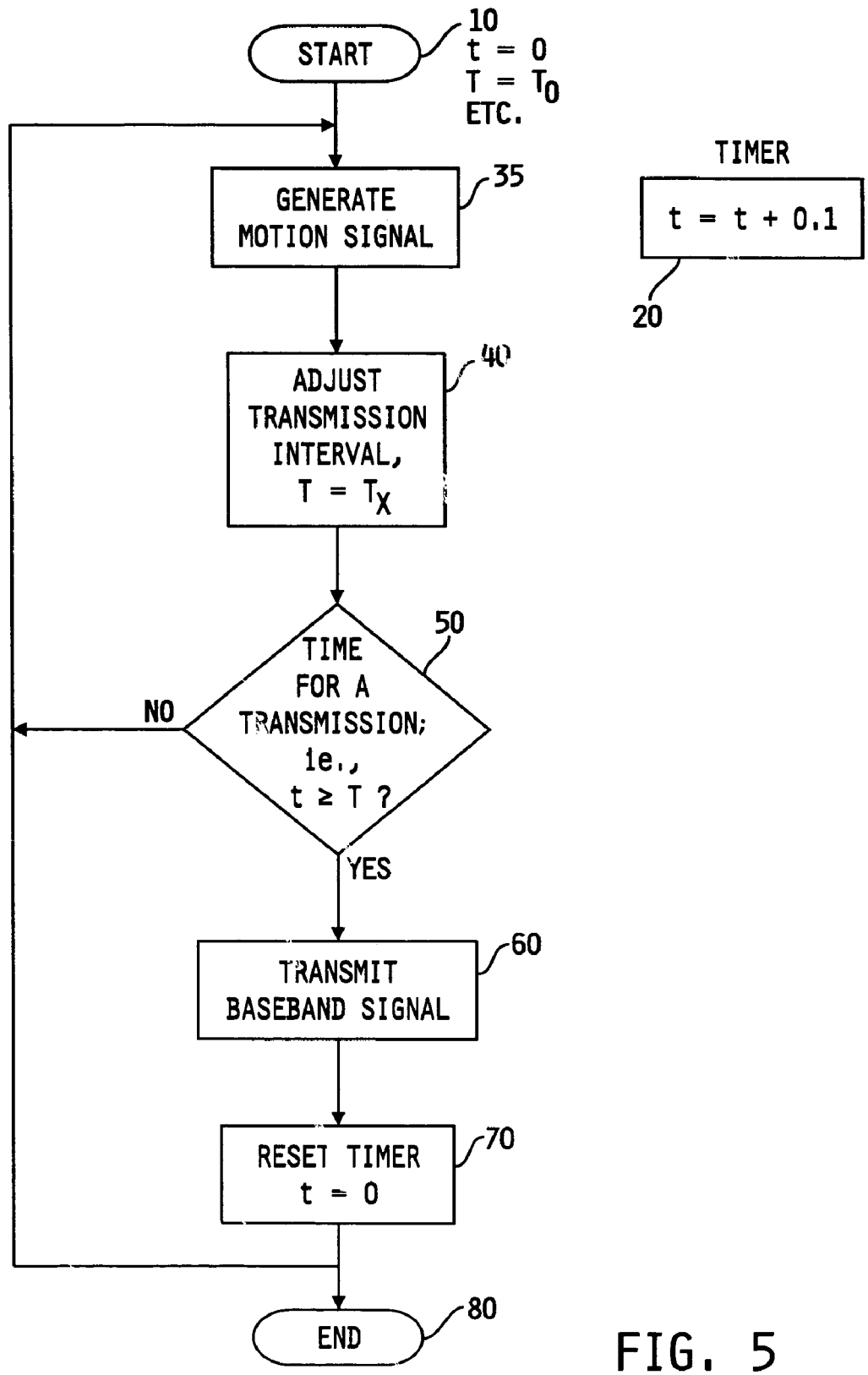
FIG. 5 is a flow diagram of the operation of a badge according to the present invention.

FIG. 5 is an operational flow diagram for the badge 26 according to the present invention. Step 10 represents startup operations wherein the motion sensor 30 and the transmitter 34 reset hardware and initialize software registers to appropriate starting values. Thus, step 10 is preferably performed at power up; i.e., upon a user's installation of a fresh battery or removal of the badge 26 from a battery recharging station. After step 10, the badge 26 concurrently executes step 20 and step 35. Step 20 represents operations of a realtime timer. Here, the microcontroller 95 updates a realtime value, "t," according to principles well know in the art concurrently with other operations of the badge 26. The realtime value increment is shown as one tenth of a second, but any other suitable increment may be used.

In step 35, the motion sensor 30 generates the motion signal. As noted above, the motion sensor 30 is not limited to a direct measurement of the speed of the asset. In step 40, the microcontroller 95 receives the motion signal from the motion sensor 30 and adjusts a transmission interval, "T," which directly corresponds to the transmission rate. The transmission interval is the desired amount of time between transmissions of the information signal (see step 60) such that the locating and tracking system has the desired dynamic resolution for the speed of movement of the asset as indicated by the motion signal. To this end, the microcontroller 95 sets the transmission interval to any one of at least three different transmission intervals that correspond to the motion signal.

For example, when the asset is a nurse standing still, a condition that generates a first motion signal, the microcontroller 95 may suitably adjust the transmission interval to be, for example, one minute. When the motion signal indicates that the nurse is moving (e.g., walking) through the hospital at, for example, 3 ft/sec, the microcontroller 95 may suitably adjust the transmission interval to be 5 seconds. When the motion signal indicates that the nurse is moving (e.g., running) through the hospital at, for example, 20 ft/sec, the microcontroller 95 may suitably adjust the transmission interval to be 0.5 seconds. In any event, it is noted that the present invention is not limited to the foregoing exemplary transmission intervals, nor to exactly three different transmission intervals. The microcontroller 95 may suitably be configured to select from a plurality of transmission intervals, including an infinite number, based on any suitable relationship(s) to the motion signal. For example, the transmission intervals may be determined based on an analog relationship with the motion signal.

In step 50, the microcontroller 95 determines whether the desired time interval between transmissions has elapsed by comparing the realtime value to the transmission interval. If the time interval has elapsed, then the badge 26 proceeds to step 60; otherwise, the badge 26 loops back to step 35. In step 60, the badge 26 transmits the desired information signal as described below. The microcontroller 95 reads memory that contains an encoded Identification number and then causes the IR LEDs 92 to transmit the identification code in pulse-code modulation on the infrared carrier. After step 60, the badge 26 proceeds to step 70 where the microcontroller 95 resets the realtime value to zero so that the badge 26 can measure the time interval until the next desired transmission. After step 70, the badge 26 loops back to step 35.

In the exemplary embodiment described herein, the present invention provides asynchronous communications of data through a free-space infrared channel in infrared at a peak wavelength of 940–950 nm. According to one embodiment, the infrared signal is pulse code modulated ("PCM") in pulses of a fixed amplitude at a carrier frequency of 455 kHz, +/−2300 Hz with a 50% positive carrier duty cycle. However, it should be readily appreciated that the various particulars of data transmission according to the present invention may be implemented via other peak wavelengths, pulse amplitude modulation ("PAM"), frequency modulation (FM) or any other suitable modulation, a different duty cycle, and/or any other suitable schemes.

Figures 6, 7, 8:
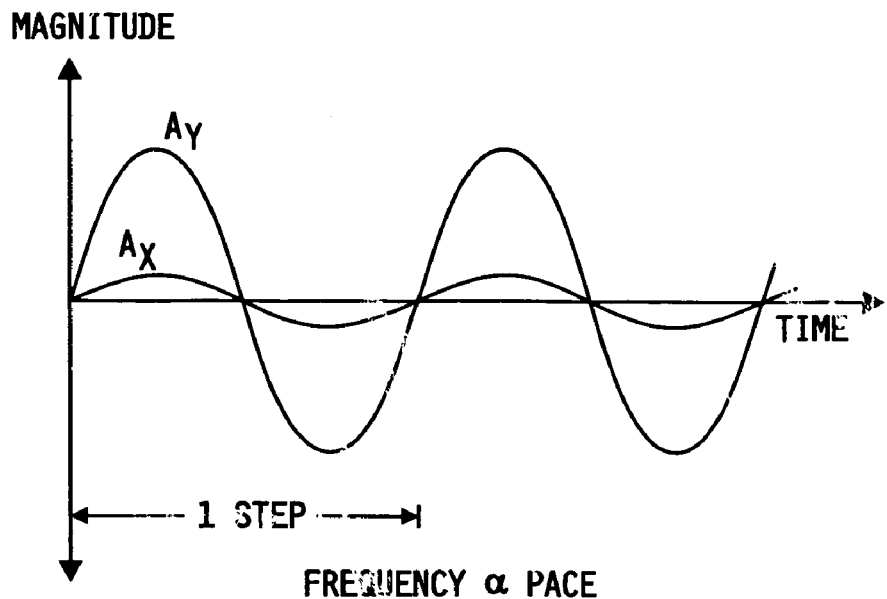

FIG. 6 shows an exemplary vertical acceleration curve, "$A_y$," and an exemplary horizontal acceleration curve, "$A_x$," generated by the motion sensor 30. $A_y$ and $A_x$ may correspond to a walking or running nurse 11 with the badge 26 attached to his or her clothing. Since walking and running are fairly rhythmic motions, the badge 26 is accelerated vertically and horizontally in a generally periodic manner. Each step or stride taken by the nurse 11 is detectable as the period of $A_y$. Thus, the frequency of $A_y$ is proportional to the number of steps taken by the nurse 11 per unit of time, which is proportional to the approximate pace at which the nurse 11 walks or runs through the hospital.

As a result of the above-described movement, the microcontroller 95 receives a PCM indication of $A_y$ in the motion signal from the dual axis accelerometer 90. The microcontroller 95 then determines the approximate speed of movement of the nurse 11 by demodulating the motion signal and determining the frequency of $A_y$. Further, the microcontroller 95 suitably varies the transmission interval of the information signal as a function of the frequency of $A_y$. Finally, the microcontroller 95 causes the desired periodic transmission of the information signal at a transmission interval that corresponds to the motion signal. As should be apparent from the foregoing, the badge 26 transmits the identification signals more frequently as the speed of the asset increases. Therefore, the locating and tracking system is able to maintain more accurate data regarding the actual location of the asset.

Additionally, in the case of a wheeled asset or an asset on skids (for example: a hospital bed, a cart, a table, etc.), the accelerations imparted to the badge 26 should also be fairly periodic, corresponding to each revolution of the wheel(s) or vibrations of the skid(s). In the case of a wheeled asset, the detection of acceleration may be enhanced by adding a ridge or a bump to a wheel of the asset. In any event, although the relationship of $A_y$, $A_x$, and time may vary among different types of assets, the periodic nature of the accelerations imparted to the badge 26 while the asset is in motion should be readily discernable via the appropriate signal processing algorithms. Moreover, as noted above, the motion sensor 30 may readily be configured to generate the motion signal based on any other parameter that varies with the speed of movement of the asset. For example, for wheeled assets, the motion sensor 30 may be a conventional speedometer.

FIGS. 7–10 show details regarding an exemplary transmission protocol for an information signal according to the present invention. FIG. 7 and FIG. 8 show signals, corresponding to a logical 1 ("HI") and logical 0 ("LO"), respectively, of the information signal. Each data bit, regardless of whether it is a HI or LO, is twelve pulse cycles in duration (or approximately 26.4 $\mu$sec). The HI bit includes twelve pulses of the 455 kHz (2.2 $\mu$sec/cycle) carrier prior to demodulation. The LO bit is characterized by the absence of such pulses.

FIG. 9 shows a total bit time for one data bit of the information signal. The total bit time (66 $\mu$sec) is the sum of the bit ON time (26.4 $\mu$sec) and a bit spacing (or "bit OFF" time) (39.6 $\mu$sec). Accordingly, the positive data bit duty cycle is the bit ON time (26.4 $\mu$sec) divided by the total bit time (66 $\mu$sec), or approximately 40%. However, it should be noted that any suitable bit ON time and/or bit spacing may be employed, resulting in a correspondingly different positive data bit duty cycle.

FIG. 10 shows a message packet and communication protocol for the information signal. The message packet illustrated in FIG. 10 corresponds to an identification number of 23149 (or 5A6D hexadecimal), remote notification activated, and low battery detected. In general, each message packet includes thirty-seven bits, which are transmitted in the following order (from first transmitted to last transmitted):

a start bit; a framing bit; a first set of eight identification bits (LO Byte of Identification number; i.e. LSB to bit #8); a first parity bit (odd parity error check for the first 8 Identification number bits); a second set of eight identification bits (HI Byte of Identification number; i.e bit #9 to MSB); a second parity bit (odd parity error check for the second 8 Identification number bits); a set of three remote notification bits (activation sets all 3, deactivation clears all); a third parity bit (odd parity error check for the 3 notification bits); a set of three low battery bits (activation sets all 3, deactivation clears all); a fourth parity bit (odd parity error check for 3 low battery bits); a set of three device type bits; a fifth parity bit (odd parity error check for device type bits); a set of three miscellaneous bits; a sixth parity bit (odd parity error check for miscellaneous bits); and a stop bit. Since the total bit time is 66 $\mu$sec, the total message packet transmission time is 2.442 msec (66 $\mu$sec×37 bits), and the effective data transmission rate is approximately 15 k baud (1 second/ 66 $\mu$sec=15,151).

According to the above-described protocol, three bits (the start bit, the framing bit, and the stop bit) are synchronization bits that ensure that the transmitter and the receiver are synchronized for proper communication of the message packet. In one embodiment, each synchronization bit is always HI, and follows a signal scheme that is identical to that discussed above in connection with the data bits (see FIGS. 7–9). The protocol also includes six parity bits for the data that immediately precedes each parity bit which also preferably follow the signal scheme of the data bits. Preferably, the parity is odd for all six parity bits. In other words, when an even number of HI data bits is transmitted after the last synchronization bit or the last party bit, the following parity bit is HI. When an odd number of HI data bits is transmitted after the last synchronization bit or the last party bit, the following parity bit is LO. Thus, the sum of the number of HI data bits transmitted after the last synchronization bit or party bit and the number of HI bits represented by the parity bit, i.e., one HI bit if the parity bit is HI and zero HI bits if the parity bit is LO) should always be an odd number. Accordingly, zero HI data bits corresponds to an even number of HI data bits.

The remaining twenty-eight bits are data bits. As indicated in the above list, the data bits include information regarding various locations and/or status of hospital personnel and/or equipment, such as an identification number to indicate the presence of a particular nurse or other staff member, or an intravenous cart, or other piece of equipment. In the exemplary protocol, the first set of eight data bits communicate a low byte (least significant eight bits, or "LSB") of an identification number (or "ID"), and the second set of eight data bits communicate a high byte (most significant eight bits, or "MSB") of the ID. It should be readily appreciated that the resulting sixteen bit binary ID allows for 65,535 unique indicators.

The remote notification may communicate that the nurse identified by the ID requires assistance, that the equipment identified by the ID requires maintenance or has completed an automated task, or any other suitable alert or status. Preferably, a remote notification is indicated by transmitting fifteen message packets wherein the three remote notification bits are HI in all fifteen of the message packets. In the illustrated embodiment, the remote notification bits return LO following the fifteen repetitions (until the remote notification feature is activated again).

Using the protocol of FIG. 10, a low battery condition of transmitter 34 is communicated by repeatedly transmitting message packets wherein the three low battery bits remain HI. The three device type bits are used to communicate one of eight different categories, priorities, classes, or the like for the ID transmitted in the same message packet. The different classifications may be treated differently under any number of various hospital operating procedures. For example, doors to laboratory facilities may be automatically locked or unlocked depending on whether a nurse or a visitor is identified. Further, the categorization of the IDs allows priority tracking of particular categories over others when the monitoring system is fully taxed. For example, when the number of visitors in the hospital begins to push a personnel locating system beyond its full capacity, nurses and/or staff may be temporarily dropped off the system. Additionally, the device type bits allow a personnel locating system to use different "exit timer" settings, whereby a central control station may automatically indicate that different IDs have left their last known areas when the numbers have not been transmitted for different "exit times." For example, a system may indicate that a food service person has left a particular patient's room when his or her ID is not transmitted from the room for one minute, while not automatically indicating that a nurse has left the room until after his or her ID is not transmitted for five or ten minutes. By providing different categories of identification members, the device type bits may be used to effectively multiply the number of available IDs by a factor of eight.

The three miscellaneous bits may suitably be used for any suitable personnel and/or equipment locating, tracking, and/or status feature(s).

Figure 11:
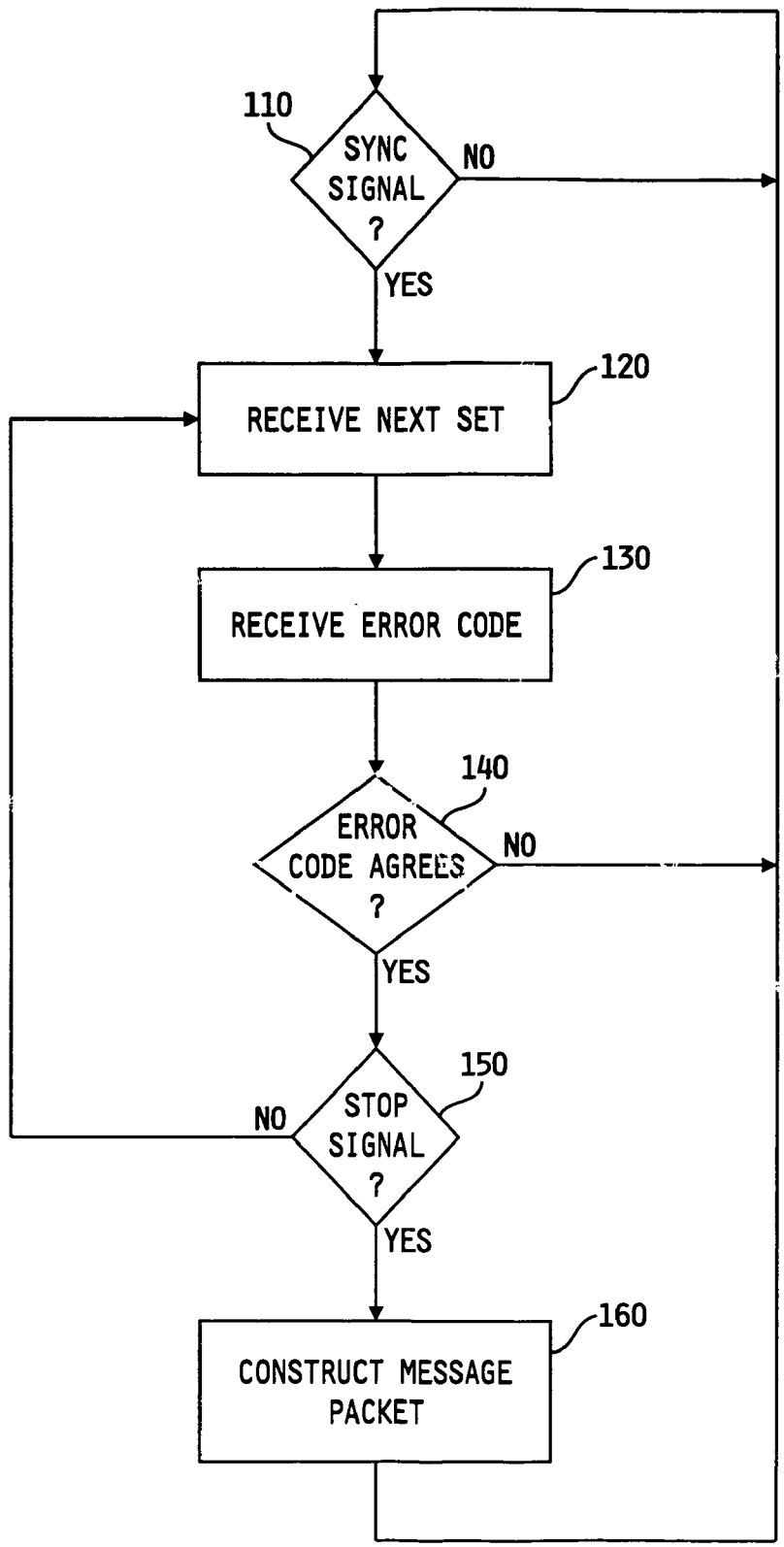
FIG. 11 is a flow diagram of an exemplary transmission error handling scheme according to the present invention.

Referring now to FIG. 11, a transmission error handling scheme is shown which, in addition to the variable transmission interval of the present invention, enhances the overall dynamic resolution of the hospital locating and tracking system by increasing the likelihood that the information signals from the badge 26 are properly received by the system receivers (for example, the patient station 18 of FIG. 4). The error handling scheme assumes a transmission protocol identical or similar to that shown in FIG. 10, in which parity bits or other error codes are interwoven into the message packet between sets of data bits. In step 110, the receiver checks for the reception of a synchronization signal such as a start bit and/or a framing bit, or any other suitable asynchronous communications synchronization signal. The receiver continuously performs step 110 until a synchronization signal is received. After receiving a synchronization signal, the receiver receives the next set of data bits (step 120). For example, in FIG. 10, the next set of data bits after the synchronization signal is preferably the LO Byte of the identification code. The set of data bits after the parity bit that follows the LO Byte is preferably the HI Byte of the identification code. In step 130, the receiver receives an error code such as a parity bit or other suitable error code. In FIG. 10, the error code following the first set of data bits is the first parity bit (between the LO Byte and the HI Byte of the identification code). In step 140, the receiver determines whether the error code received in step 130 agrees with the data bits received in step 120. If not, then the receiver loops back to step 110 (discussed above). Therefore, once the receiver finds an error, the receiver automatically begins looking for the next valid transmission signal. This decreases the likelihood that the receiver will miss a valid signal.

If the error code of step 130 agrees with the data bits of step 120, then the receiver determines whether a stop signal for the incoming asynchronous communications from the badge 26 has been detected (step 150). If not, then the receiver loops back to step 120 (discussed above) to continue receiving data bits. Upon receipt of a stop signal, the receiver constructs a message packet (step 160) such as that shown in FIG. 10 that includes the sets of data bits received prior to the receipt of the stop signal in step 150. After step 160, the receiver loops back to step 110 (discussed above).

By executing the error handling scheme shown in FIG. 11, the receiver avoids being unnecessarily "tied up" by erroneous message packets or ambient noise. In other words, environmental noise that could otherwise be interpreted as the initiation of a transmission from the badge 26 does not require the receiver to wait for a timeout period that must be in excess of the total message packet length. Instead, the receiver disregards an incoming transmission as soon as it determines that the error code for a particular set of data bits within the expected message packet disagrees with its corresponding set of data bits. As a result, the receiver "resets" (becomes ready to receiver a proper transmission from the badge 26) much sooner than it would were it to wait for the expiration of a timeout period in excess of the total message packet time. Thus, a moving asset in a noisy environment is less likely to "skip" or "jump over" the receiver, thereby enhancing the overall dynamic resolution of the system.

The foregoing description of the invention is illustrative only, and is not intended to limit the scope of the invention to the precise forms set forth. Although the invention has been described in detail with reference to certain illustrative embodiments, variations and modifications exist within the scope and spirit of the invention as described and defined in the following claims.

What is claimed is:

1. A badge configured to locate and track an asset in a hospital, the badge comprising:
a motion sensor configured to generate a first signal that corresponds to a speed of movement of the asset through the hospital; and
a transmitter coupled to the motion sensor to receive the first signal therefrom, the transmitter being further configured to periodically transmit a second signal at any one of at least three different transmission intervals that correspond to the first signal.

2. The badge of claim 1, wherein the motion sensor includes an accelerometer that is configured to respond to an acceleration of the asset.

3. The badge of claim 2, wherein the motion sensor is further configured to include in the first signal a plurality of pulses having a duty cycle that is proportional to the acceleration of the asset.

4. The badge of claim 1, wherein the motion sensor includes a first accelerometer that is configured to respond to a first acceleration of the asset along a first axis and a second accelerometer that is configured to respond to a second acceleration of the asset along a second axis.

5. The badge of claim 4, wherein the motion sensor is further configured to include a plurality of first pulses in the first signal, the first pulses having a first duty cycle proportional to the first acceleration of the asset.

6. The badge of claim 5, wherein the motion sensor is further configured to include a plurality of second pulses in the first signal, the second pulses having a second duty cycle proportional to the second acceleration of the asset.

7. The badge of claim 1, wherein the transmitter is further configured to include an identification code in the second signal.

8. The badge of claim 1, wherein the transmitter is further configured to transmit the second signal on an infrared carrier.

9. The badge of claim 1, wherein the transmitter is further configured to transmit the second signal on a radio frequency carrier.

10. The badge of claim 1, wherein the transmission intervals have an analog relationship to the first signal.

11. The badge of claim 1, wherein the transmitter includes a controller coupled to the motion sensor, the controller being operable to vary the transmission interval based on the speed of movement of the asset.

12. The badge of claim 1, wherein the second signal includes a plurality of sets of data bits, each set of data bits having an associated error code for detecting errors in transmission of the second signal.

13. A system configured to locate and track an asset in a hospital, the system comprising:
a motion sensor configured to generate a motion signal that corresponds to a speed of movement of the asset through the hospital, the motion sensor including a first accelerometer that is configured to respond to a first acceleration of the asset along a first axis and a second accelerometer that is configured to respond to a second acceleration of the asset along a second axis, the motion sensor further configured to include in the motion signal a plurality of first pulses having a duty cycle that is proportional to the first acceleration of the asset and a plurality of second pulses having a duty cycle that is proportional to the second acceleration of the asset; and
a transmitter coupled to the motion sensor to receive the motion signal therefrom, the transmitter being further configured to periodically transmit an identification code on an infrared carrier at any one of at least three different transmission intervals that correspond to the motion signal.

14. The system of claim 13, wherein the motion sensor and the transmitter are mounted to a badge, the badge including a fastener being removably connectable to the asset.

15. The system of claim 13, further including a plurality of receivers configured to receive the identification code.

16. A method for locating and tracking an asset in a hospital, the method comprising the steps of:
generating a first signal that corresponds to a speed of movement of the asset through the hospital; and
periodically transmitting a second signal at any one of at least three different transmission intervals that correspond to the first signal.

17. The method of claim 16, wherein the step of generating the first signal includes the step of responding to an acceleration of the asset.

18. The method of claim 17, wherein the step of responding to an acceleration of the asset includes the step of generating a plurality of pulses having a duty cycle that is proportional to the acceleration of the asset.

19. The method of claim 16, wherein the step of generating the first signal includes the steps of:
responding to a first acceleration of the asset along a first axis; and
responding to a second acceleration of the asset along a second axis.

20. The method of claim 19, wherein the step of generating the first signal further includes the step of generating a plurality of first pulses having a first duty cycle that is proportional to the first acceleration of the asset.

21. The method of claim 20, wherein the step of generating the first signal further includes the step of generating a plurality of second pulses having a second duty cycle that is proportional to the second acceleration of the asset.

22. The method of claim 16, wherein the step of periodically transmitting the second signal includes the step of generating an identification code.

23. The method of claim 16, wherein the step of periodically transmitting the second signal includes the step of generating an infrared carrier.

24. The method of claim 16, wherein the step of periodically transmitting the second signal includes the step of generating a radio frequency carrier.

25. The method of claim 16, wherein the transmission intervals are related to the first signal according to an analog function.

26. A badge for locating and tracking a hospital asset, including:
a motion sensor coupled to the asset that generates a first motion signal when the asset moves at a first speed and a second motion signal when the asset moves at a second speed; and
a transmitter coupled to the motion sensor, the transmitter transmitting an information signal at a first transmission rate in response to the first motion signal and at a second transmission rate in response to the second motion signal.

27. The badge of claim 26, wherein the motion sensor includes an accelerometer configured to respond to an acceleration of the asset.

28. The badge of claim 26, wherein the motion sensor includes a first accelerometer that detects acceleration of the asset along a first axis, and a second accelerometer that detects acceleration of the asset along a second axis.

29. The badge of claim 26, wherein each of the first and the second motion signals includes a first plurality of pulses having a first duty cycle that is proportional to a first acceleration of the asset along a first axis, and a second plurality of pulses having a second duty cycle that is proportional to a second acceleration of the asset along a second axis.

30. The badge of claim 26, wherein the information signal includes a unique identification code that identifies the badge.

31. A badge for locating and tracking a hospital asset, including:

a motion sensor carried by the asset that generates a motion signal when the asset is in motion, the motion signal varying with changes in the speed of the moving asset; and a transmitter coupled to the motion sensor that transmits an information signal at a transmission rate that varies as a function of the variable motion signal.

32. The badge of claim 31, wherein the motion sensor includes a first accelerometer that detects acceleration of the asset along a first axis, and a second accelerometer that detects acceleration of the asset along a second axis.

33. The badge of claim 31, wherein the motion signal includes a first plurality of pulses having a first duty cycle that is proportional to a first acceleration of the asset along a first axis, and a second plurality of pulses having a second duty cycle that is proportional to a second acceleration of the asset along a second axis.

34. The badge of claim 31, wherein the information signal includes a unique identification code that identifies the badge.

* * * * *